US00PP12750P2

(12) United States Plant Patent
Lommerse

(10) Patent No.: US PP12,750 P2
(45) Date of Patent: Jul. 2, 2002

(54) DAHLIA PLANT NAMED 'DAHLSTAR SALMON'

(75) Inventor: Henry Lommerse, Mariahout-Laarbeek (NL)

(73) Assignee: Kieft Seed Holland, Venhuizen (NL)

( * ) Notice: Subject to any disclaimer, the term of this patent is extended or adjusted under 35 U.S.C. 154(b) by 1 days.

(21) Appl. No.: 09/795,468

(22) Filed: Mar. 1, 2001

(51) Int. Cl.[7] ..... A01H 5/00
(52) U.S. Cl. ..... Plt./321
(58) Field of Search ..... Plt./321

(56) References Cited

PUBLICATIONS

GTITM UPOVROM Citation for 'Dahlstar Salmon' as per NL PBR DHL0083; Jul. 22, 1997.*

* cited by examiner

*Primary Examiner*—Kent L. Bell
(74) *Attorney, Agent, or Firm*—C. A. Whealy

(57) ABSTRACT

A distinct cultivar of Dahlia plant named 'Dahlstar Salmon', characterized by its upright and compact plant habit; freely branching, full and dense plants; medium-sized semi-double type inflorescences; red and yellow-colored ray florets with bright yellow-colored disc florets; and good garden performance.

1 Drawing Sheet

BACKGROUND OF THE INVENTION

The present Invention relates to a new and distinct cultivar of Dahlia plant, botanically known as *Dahlia variabilis*, commercially referred to as a pot-type Dahlia, and hereinafter referred to by the cultivar named 'Dahlstar Salmon'.

The new Dahlia is a product of a planned breeding program conducted by the Inventor in Mariahout-Laarbeek, The Netherlands. The objective of the breeding program is to create new pot-type Dahlia cultivars with desirable inflorescence form, attractive colors, and good garden performance.

The new Dahlia originated from a cross made by the Inventor of two unidentified proprietary *Dahlia variabilis* selections, not patented. The new Dahlia was discovered and selected by the Inventor as a single flowering plant within the progeny of the stated cross grown in a controlled environment in Mariahout-Laarbeek, The Netherlands. Plants of the new Dahlia differ from plants of the parent selections primarily in ray floret coloration.

Asexual reproduction of the new Dahlia by vegetative tip cuttings was first conducted in Mariahout-Laarbeek, The Netherlands in 1996. Asexual reproduction by cuttings has shown that the unique features of this new Dahlia are stable and reproduced true to type in successive generations.

SUMMARY OF THE INVENTION

The cultivar 'Dahlia Salmon' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dahlstar Salmon'. These characteristics in combination distinguish 'Dahlstar Salmon' as a new and distinct pot-type Dahlia:

1. Upright and compact plant habit.
2. Freely branching, full and dense plants.
3. Medium-sized semi-double type inflorescences.

4. Red and yellow-colored ray florets with bright yellow-colored disc florets.
5. Good garden performance.

BRIEF DESCRIPTION OF THE PHOTOGRAPH

The accompanying colored photograph illustrates the overall appearance of the new Dahlia showing the colors as true as it is reasonably possible to obtain in colored reproductions of this type. Colors in the photograph may differ from the color values cited in the detailed botanical description which accurately describe the colors of the new Dahlia. The photograph comprises a side perspective view of a typical flowering plant of 'Dahlstar Salmon'.

DETAILED BOTANICAL DESCRIPTION

In the following description, color references are made to The Royal Horticultural Society Colour Chart except where general terms of ordinary dictionary significance are used. The following observations and measurements describe plants grown and flowered during the spring in Venhuizen, The Netherlands, in a glass-covered greenhouse and with conditions which approximate those generally used in commercial production. One rooted cutting was planted in a 10-cm container and pinched about one week after planting. During the production time, the following environmental conditions were maintained: day temperatures, about 18 to 21° C.; night temperatures, about 15 to 18° C.; and light levels about 40,000 lux. Measurements and numerical values represent averages of typical flowering plants about 6 to 8 weeks after planting.

Botanical classification: *Dahlia variabilis* cultivar 'Dahlstar Salmon'.

Commercial classification: Pot-type Dahlia.

Parentage:

*Female, or seed, parent*.—Unidentified proprietary *Dahlia variabilis* selection, not patented.

*Male, or pollen, parent*.—Unidentified proprietary *Dahlia variabilis* selection, not patented.

Propagation:

*Type*.—Terminal tip cuttings.

*Time to rooting*.—About 10 to 12 days at 22° C.

*Time to develop a rooted cutting*.—About 21 to 24 days at 22° C.

*Root description*.—Fine, fibrous and well-branched; development of tubers has not been observed.

Plant description:

*Appearance*.—Herbaceous pot-type Dahlia. Inverted triangle; stems mostly upright and somewhat outwardly spreading giving a uniformly mounded appearance to the plant; relatively compact. Freely branching, lateral branches develop at every node after removal of terminal apex (pinching); dense and full plants. Appropriate for 9 to 12-cm containers.

*Plant height*.—About 15 cm.

*Plant width or area of spread*.—About 12.5 cm.

*Lateral branches*.—Quantity per plant: About 15 to 20. Length: About 10 cm. Diameter: About 5 mm. Strength: Strong. Texture: Smooth, glabrous. Color: Close to 146A with anthocyanin, 183A.

*Foliage description*.—Arrangement: Leaves single or compound with three or five leaflets. Length: Single leaves: About 6 to 8 cm. Compound leaflets: About 3 to 4 cm. Width: Single leaves: About 4 to 5 cm. Compound leaflets: About 2 to 2.5 cm. Shape: Ovate. Apex: Acuminate. Base: Obtuse to cuneate. Margin: Dentate. Texture: Smooth, glabrous. Petiole length: About 1 cm. Petiole diameter: About 3 mm. Color: Young foliage, upper surface: 144A. Young foliage, lower surface: 144B. Mature foliage, upper surface: 143A; venation, 145C. Mature foliage, lower surface: 143B, venation, 145B. Petiole: 145B.

Inflorescence description:

*Appearance*.—Terminal and axillary semi-double type inflorescences held above and beyond the foliage on strong flexible peduncles. Composite inflorescence form with elongated-oblong to roughly spatulate shaped ray florets and disc florets massed at the center; ray and disc florets arranged acropetally on a capitulum. Not fragrant. Persistent.

*Flowering response*.—Plants flower continuously and freely from April until October in Northern Europe.

*Postproduction longevity*.—Inflorescences maintain good color and substance for about three to five days on the plant.

*Quantity of inforescences*.—During the flowering season, up to about 100 to 150 inflorescences per plant may develop.

*Inflorescence bud* (*just before opening*).—Shape: Mostly spherical. Length: About 5 to 10 mm. Diameter: About 5 to 10 mm. Color: Close to 144A.

*Inflorescence size*.—Diameter: About 3.5 to 4 cm. Depth (height): About 1.5 cm. Diameter of disc: About 7 to 8 mm.

*Ray florets*.—Shape: Elongated-oblong to roughly spatulate. Aspect: Straight, concave. Length: About 1.5 cm. Width: About 1 cm. Apex: Acute to obtuse, occasionally retuse. Base: Attenuate; short to medium corolla tube. Margin: Entire. Texture: Smooth, glabrous, velvety. Number of ray florets per inflorescence: About 42 in about four or five rows. Color: When opening and fully opened, upper surface: Towards apex, 44A to 42A; towards base, 9A; fading to 12A with subsequent development. When opening and fully opened, lower surface: Towards apex, 44A to 42A; towards base, 9A.

*Disc florets*.—Shape: Tubular, elongated. Apex: Five-pointed. Length: About 8 mm. Width: Apex, about 1.5 mm; base, about 1 mm. Number of disc florets per inflorescence: About 24. Color: Immature: 154A. Mature: Apex: 9A to 12A. Base: 155D.

*Involucral bracts*.—Quantity: About 5 to 7, imbricate. Length: About 1 to 1.25 cm. Width: About 7 mm. Shape: Roughly deltoid. Apex: Acute. Margin: Entire. Texture: Smooth, leathery. Color: Close to 146A, both surfaces.

*Peduncles*.—Length, terminal inflorescence: About 3 to 5 cm. Diameter: About 3 mm. Strength: Strong, very flexible. Color: 139A with anthocyanin, 59B.

*Reproductive organs*.—Androecium: Present on disc florets only. Anther color: 9A. Pollen amount: Abundant. Pollen color: 9A. Gynoecium: Present on both ray and disc florets.

*Seed*.—Seed production has not been observed.

Disease tolerance: Plants of the new Dahlia have been observed to be tolerant to Powdery Mildew.

Weather tolerance: Plants of the new Dahlia have been observed to be wind and rain-tolerant; and have been observed to be tolerant to temperatures ranging from 12 to 30° C.

It is claimed:

1. A new and distinct cultivar of Dahlia plant named 'Dahlstar Salmon', as illustrated and described.

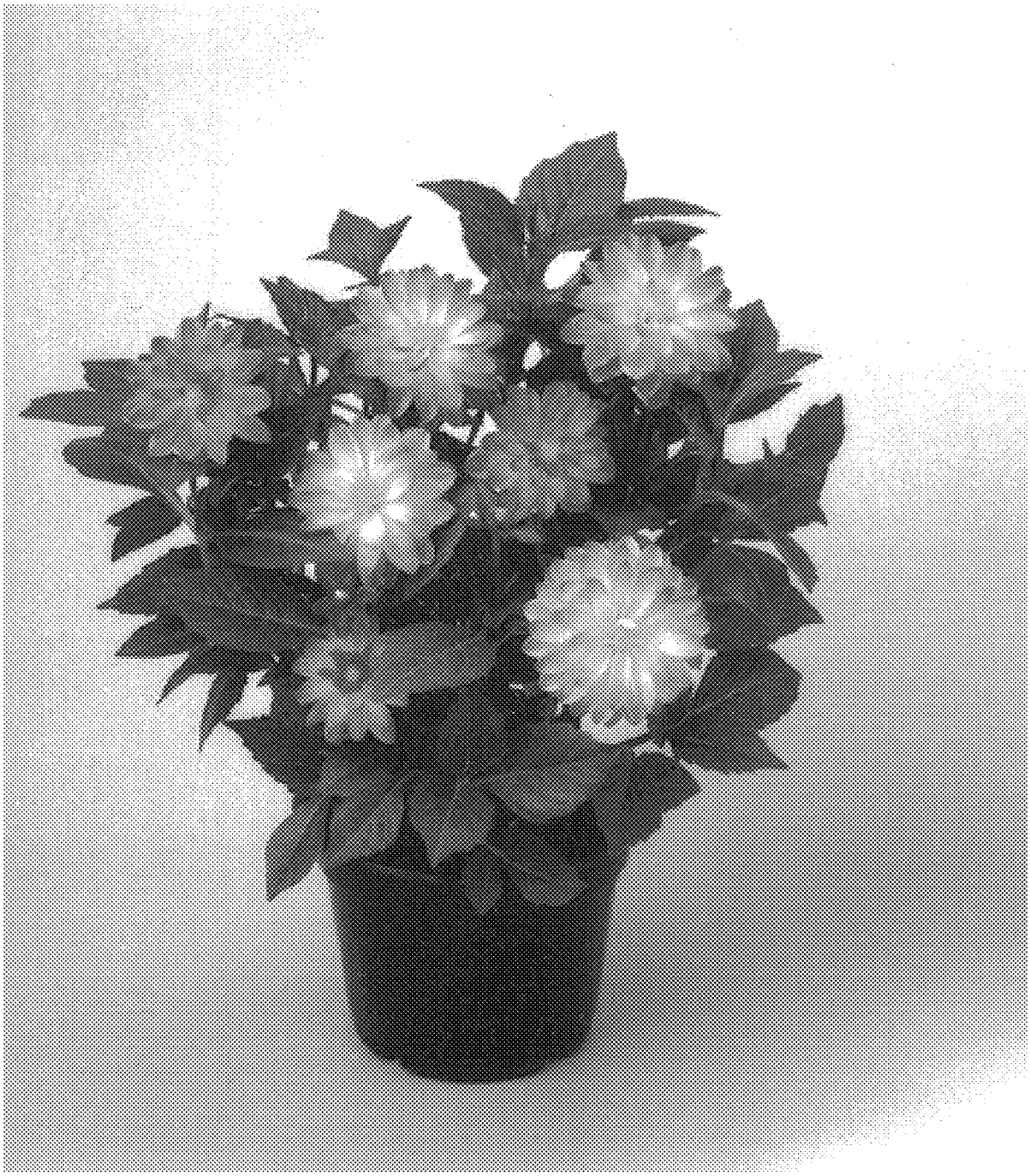

* * * * *